(12) United States Patent
Wellings et al.

(10) Patent No.: US 11,813,167 B2
(45) Date of Patent: Nov. 14, 2023

(54) PATELLOFEMORAL IMPLANT

(71) Applicant: Howmedica Osteonics Corp., Mahwah, NJ (US)

(72) Inventors: Peter Wellings, Somerset, NJ (US); Sandeep K. Chauhan, Plumpton Green (GB); Michael C. Ferko, Warwick, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 193 days.

(21) Appl. No.: 15/979,712

(22) Filed: May 15, 2018

(65) Prior Publication Data

US 2018/0325685 A1    Nov. 15, 2018

Related U.S. Application Data

(60) Provisional application No. 62/506,166, filed on May 15, 2017.

(51) Int. Cl.
*A61F 2/38* (2006.01)
*A61F 2/30* (2006.01)

(52) U.S. Cl.
CPC .......... *A61F 2/3859* (2013.01); *A61F 2/3877* (2013.01); *A61F 2002/30242* (2013.01);
(Continued)

(58) Field of Classification Search
CPC ...... A61F 2/3859; A61F 2/30942; A61F 2/38; A61F 2002/30327; A61F 2/3886;
(Continued)

(56) References Cited

U.S. PATENT DOCUMENTS 4,309,778 A * 1/1982 Buechel ............... A61F 2/4202
                                              623/20.29
5,011,496 A * 4/1991 Forte ................... A61F 2/3886
                                              623/20.26
(Continued)

FOREIGN PATENT DOCUMENTS

EP     1738720 A2    1/2007
FR     2682287 A1    4/1993
(Continued)

OTHER PUBLICATIONS

Extended Search Report from EP18172274, dated Sep. 25, 2018, pp. 1-2.

*Primary Examiner* — Ann Schillinger
(74) *Attorney, Agent, or Firm* — Lerner David LLP

(57) ABSTRACT

A femoral implant for articulation with a patella or a patellar implant includes a body having an articular surface defining a trochlear groove. The trochlear groove is defined by a first trochlear radius at a first location along the trochlear groove and by a second trochlear radius at a second location along the trochlear groove, the first radius being different than the second radius. The configuration of the trochlear groove is such that it narrows as a patella or patellar implant moves from an extension configuration to a flexion configuration. A kit includes the femoral implant along with a patellar implant. A method of trialing involves use of the femoral implant or kit to ensure a smooth transition of the patella or the patellar implant from the femoral component to the adjacent bone.

12 Claims, 9 Drawing Sheets

(52) U.S. Cl.
CPC ............... *A61F 2002/30327* (2013.01); *A61F 2002/30383* (2013.01)

(58) Field of Classification Search
CPC ............ A61F 2/3877; A61F 2002/3863; A61F 2/461; A61F 2002/30616; A61F 2002/30943; A61F 2002/30242; A61F 2002/30383
See application file for complete search history.

(56) References Cited

U.S. PATENT DOCUMENTS

| | | | |
|---|---|---|---|
| 5,413,116 A | 5/1995 | Radke et al. | |
| 5,533,519 A | 7/1996 | Radke et al. | |
| 5,593,450 A | 1/1997 | Scott et al. | |
| 6,616,696 B1 * | 9/2003 | Merchant | A61F 2/38 623/20.18 |
| 6,709,460 B2 * | 3/2004 | Merchant | A61F 2/3877 623/20.18 |
| 7,387,644 B2 | 6/2008 | Beynnon et al. | |
| 7,806,898 B2 | 10/2010 | Justin et al. | |
| 8,002,839 B2 * | 8/2011 | Rochetin | A61F 2/38 623/20.14 |
| 8,142,509 B2 | 3/2012 | McKinnon et al. | |
| 8,236,060 B2 | 8/2012 | Justin et al. | |
| 8,236,061 B2 | 8/2012 | Heldreth et al. | |
| 8,282,685 B2 | 10/2012 | Rochetin et al. | |
| 8,475,535 B2 * | 7/2013 | Otto | A61F 2/38 623/20.31 |
| 8,480,754 B2 | 7/2013 | Bojarski et al. | |
| 8,506,639 B2 * | 8/2013 | Hayden | A61F 2/3877 623/20.14 |
| 8,556,983 B2 | 10/2013 | Bojarski et al. | |
| 8,652,210 B2 * | 2/2014 | Otto | A61F 2/3886 623/20.35 |
| 8,771,365 B2 | 7/2014 | Bojarski et al. | |
| 8,777,875 B2 | 7/2014 | Park | |
| 8,911,502 B2 | 12/2014 | Li et al. | |
| 8,926,706 B2 | 1/2015 | Bojarski et al. | |
| 8,974,539 B2 | 3/2015 | Bojarski et al. | |
| 9,020,788 B2 | 4/2015 | Lang et al. | |
| 9,320,616 B2 | 4/2016 | Samuelson et al. | |
| 9,320,620 B2 | 4/2016 | Bojarski et al. | |
| 9,358,117 B2 | 6/2016 | Collazo et al. | |
| 9,387,079 B2 | 7/2016 | Bojarski et al. | |
| 9,402,729 B2 | 8/2016 | Otto et al. | |
| 2003/0158606 A1 | 8/2003 | Coon et al. | |
| 2005/0102032 A1 * | 5/2005 | Beynnon | A61F 2/38 623/20.19 |
| 2005/0143833 A1 * | 6/2005 | Merchant | A61B 17/1767 623/20.31 |
| 2006/0142657 A1 | 6/2006 | Quaid et al. | |
| 2006/0190086 A1 | 8/2006 | Clemow et al. | |
| 2008/0058945 A1 | 3/2008 | Hajaj et al. | |
| 2008/0300689 A1 * | 12/2008 | McKinnon | A61F 2/3877 623/20.2 |
| 2009/0222103 A1 | 9/2009 | Fitz et al. | |
| 2009/0228111 A1 * | 9/2009 | Otto | A61F 2/38 623/20.31 |
| 2010/0174379 A1 * | 7/2010 | McMinn | A61F 2/4657 623/20.35 |
| 2011/0087332 A1 | 4/2011 | Bojarski et al. | |
| 2011/0144760 A1 * | 6/2011 | Wong | A61F 2/4657 623/20.14 |
| 2011/0218635 A1 | 9/2011 | Amis et al. | |
| 2012/0172993 A1 * | 7/2012 | Wright | A61F 2/3877 623/20.14 |
| 2012/0172994 A1 * | 7/2012 | Wright | A61F 2/3877 623/20.18 |
| 2012/0191205 A1 | 7/2012 | Bojarski et al. | |
| 2012/0191420 A1 | 7/2012 | Bojarski et al. | |
| 2012/0209394 A1 * | 8/2012 | Bojarski | A61F 2/30942 623/20.32 |
| 2013/0204252 A1 | 8/2013 | Samuelson et al. | |
| 2013/0211531 A1 | 8/2013 | Steines et al. | |
| 2013/0226305 A1 * | 8/2013 | Donno | A61F 2/3859 623/20.35 |
| 2013/0289729 A1 | 10/2013 | Bonutti | |
| 2014/0005997 A1 | 1/2014 | Park et al. | |
| 2014/0039631 A1 | 2/2014 | Bojarski et al. | |
| 2014/0142713 A1 * | 5/2014 | Wright | A61F 2/3859 623/20.21 |
| 2014/0142714 A1 | 5/2014 | Wright et al. | |
| 2014/0228964 A1 * | 8/2014 | Lew | A61F 2/3877 623/20.18 |
| 2014/0358241 A1 * | 12/2014 | Afriat | A61F 2/3859 623/20.19 |
| 2014/0378978 A1 | 12/2014 | Park | |
| 2015/0196325 A1 | 7/2015 | Shenoy et al. | |
| 2015/0297353 A1 | 10/2015 | Amis et al. | |
| 2015/0342739 A1 | 12/2015 | Mahfouz | |
| 2015/0374386 A1 | 12/2015 | Collazo et al. | |
| 2016/0143744 A1 | 5/2016 | Bojarski et al. | |
| 2016/0217268 A1 | 7/2016 | Otto et al. | |
| 2016/0228197 A1 | 8/2016 | Park et al. | |
| 2016/0228255 A1 | 8/2016 | Samuelson et al. | |
| 2016/0235420 A1 | 8/2016 | Collazo et al. | |
| 2018/0036083 A1 | 2/2018 | Ferko et al. | |

FOREIGN PATENT DOCUMENTS

| | | |
|---|---|---|
| WO | 0170143 A1 | 9/2001 |
| WO | 2007013959 A2 | 2/2007 |
| WO | 2011071979 A2 | 6/2011 |
| WO | 2014131007 A1 | 8/2014 |
| WO | 2016026007 A1 | 2/2016 |

* cited by examiner

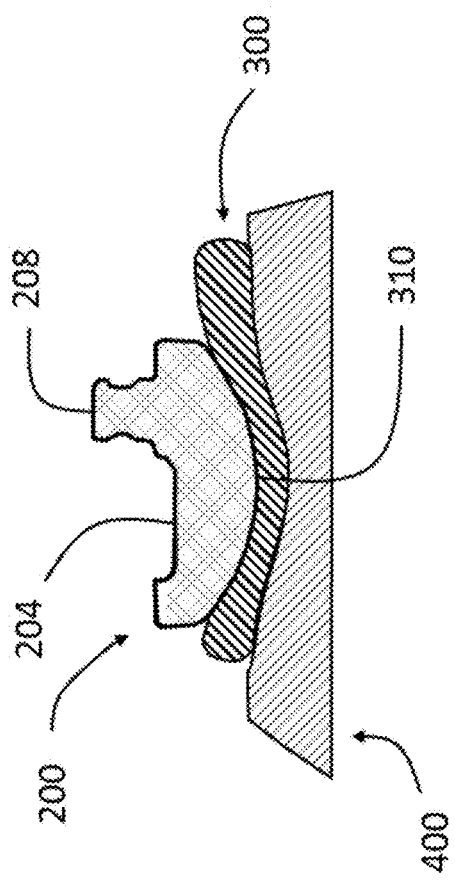
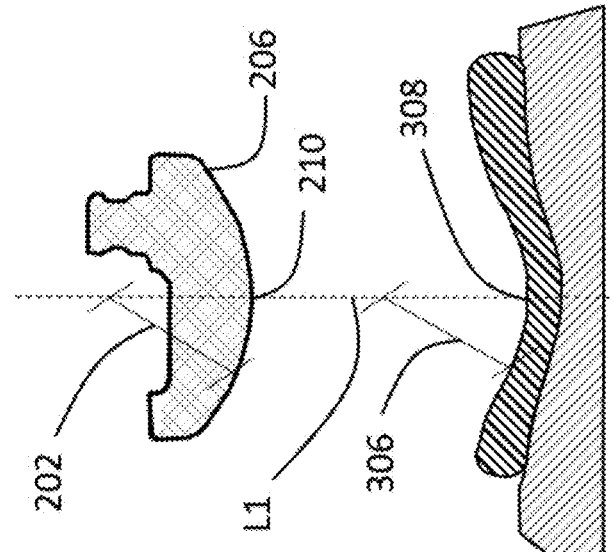
FIG. 2A
FIG. 2B

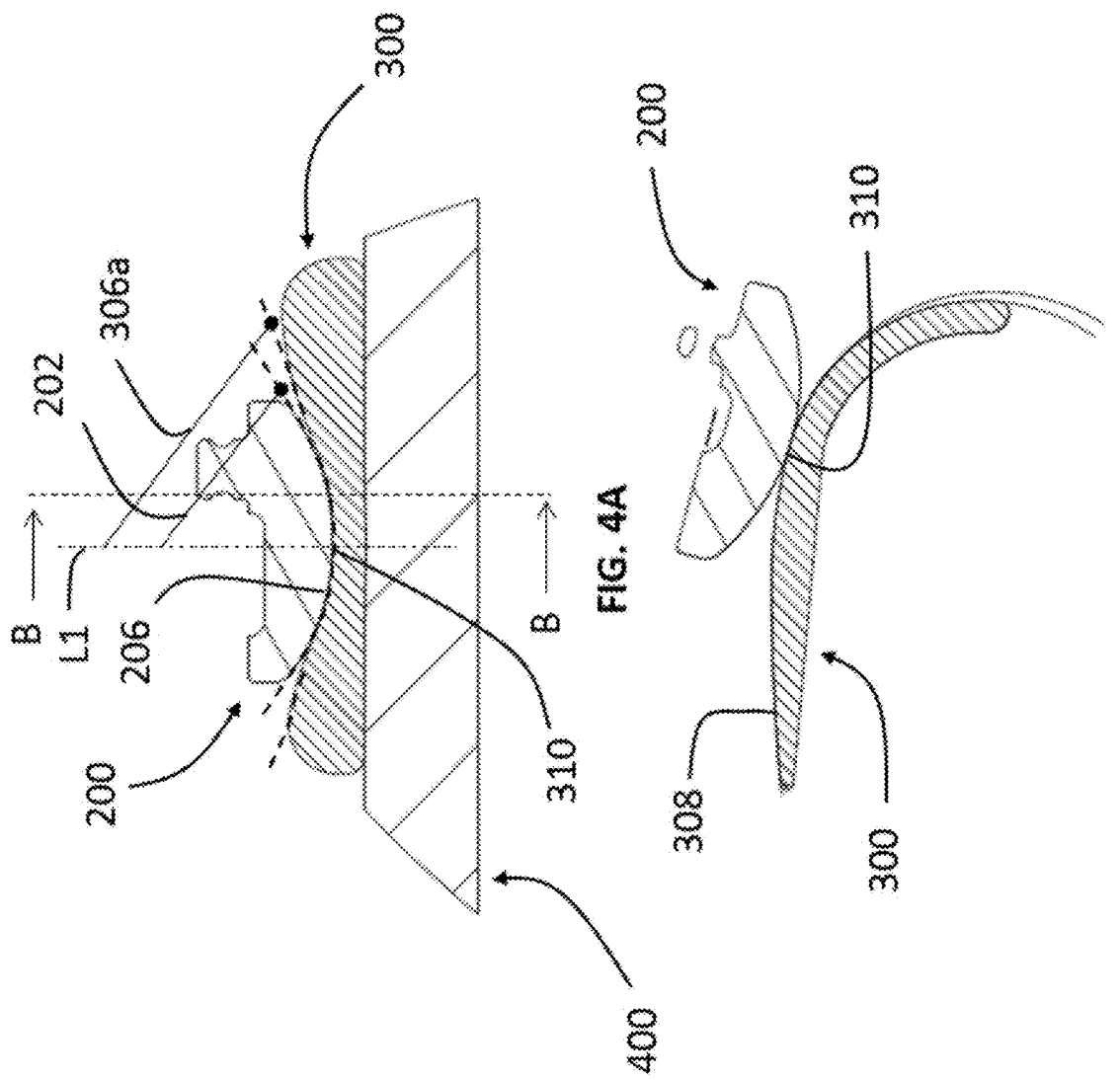

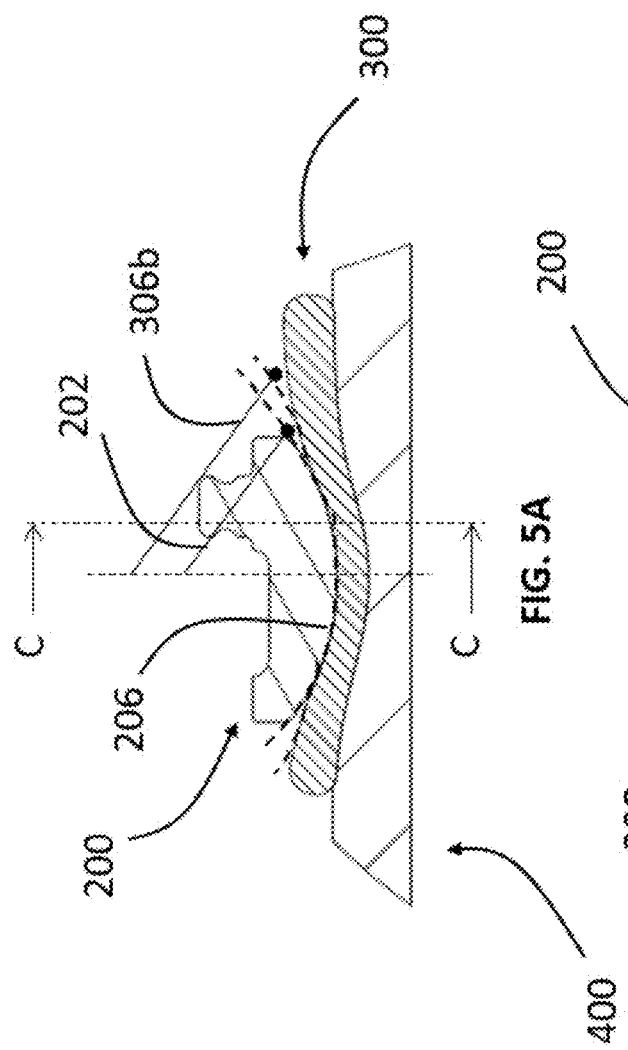

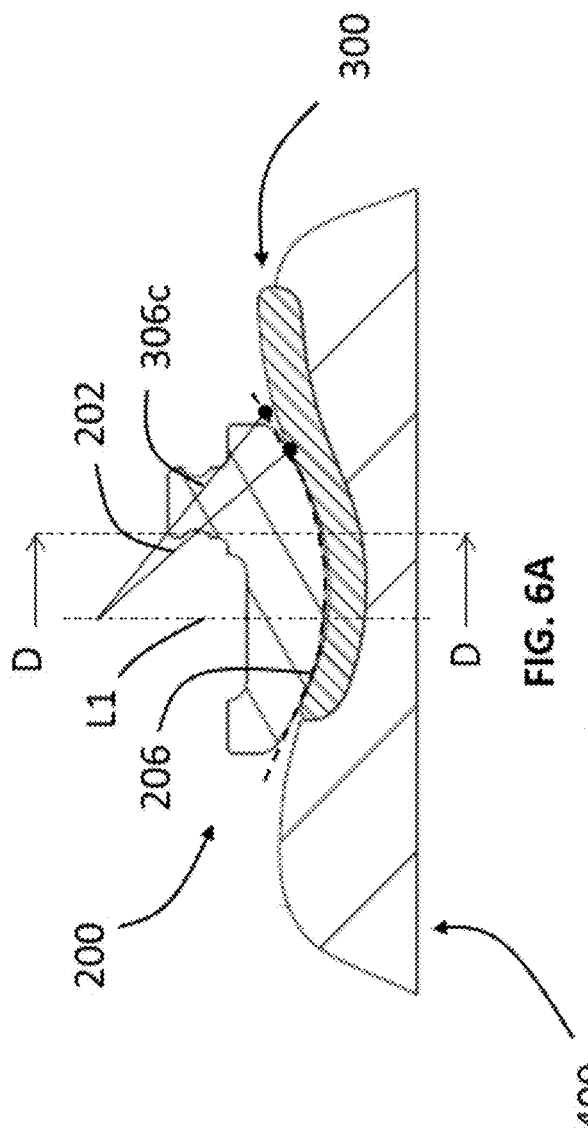
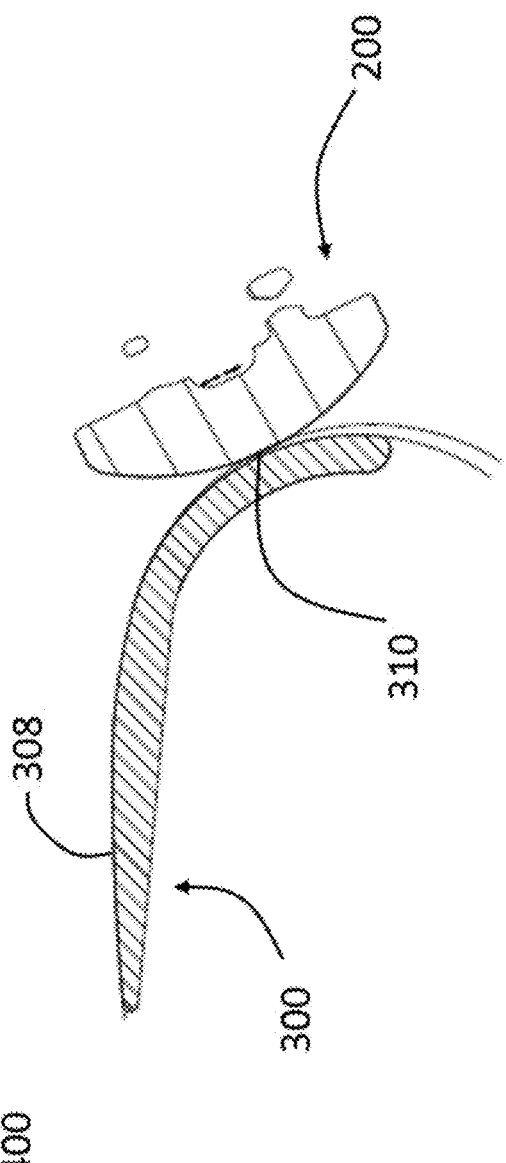
FIG. 6A
FIG. 6B

PATELLOFEMORAL IMPLANT

CROSS-REFERENCE TO RELATED APPLICATION

The present application claims the benefit of the filing date of U.S. Provisional Patent Application No. 62/506,166, filed on May 15, 2017, the disclosure of which is hereby incorporated by reference.

FIELD OF INVENTION

The present invention relates to a medical implant for bone and a method for its sizing, and in particular to a patellofemoral implant and a method for sizing the trochlear groove of the femoral component.

BACKGROUND OF THE INVENTION

Patellofemoral joint replacement is an effective alternative to total knee replacement ("TKR") for patients with isolated patellofemoral arthritis, or bicompartmental/tricompartmental disease in combination with unicompartmental knee arthroplasty. Particularly among young patients with isolated patellofemoral arthritis, patellofemoral joint replacements reduce surgical trauma and minimize the removal of healthy knee compartments and other structures which are typically required during a TKR. Advances in patellofemoral implant design have also contributed to the popularity of patellofemoral joint replacements.

A femoral prosthesis and patellar prosthesis are implanted during a patellofemoral joint replacement. The femoral prosthesis generally covers the femoral trochlear groove and may extend into the intercondylar notch. During the patellar range of motion from extension to flexion, the patellar prosthesis slides on the femoral component. Moving from mid-flexion to deep-flexion will transition the patellar prosthesis from the femoral prosthesis onto native bone, i.e., the lateral and medial condyles.

In prior art designs, the radius along the entire trochlear groove of the femoral prosthesis is designed to be larger than the corresponding radius of the patellar prosthesis so that the patellar prosthesis may be contained within the trochlear groove and may slide smoothly on the femoral prosthesis. Hence, the larger trochlear groove radius necessarily requires a central posterior surface of the articulating patellar prosthesis to be in contact with the trochlear groove during patellar motion across the femoral prosthesis. However, in such a configuration, when the patellar prosthesis transitions from the femoral prosthesis to the natural bone, the intercondylar notch does not provide support for the central posterior surface of the articulating patellar prosthesis. Instead, the patellar prosthesis is supported by the lateral and medial condyles. Even when a distal edge of the femoral prosthesis is designed to be flush with the natural bone, the patellar prosthesis abruptly transitions from a central posterior surface contact on the femoral prosthesis to a dual latera-medial contact on natural bone. This abrupt transition can lead to undesirable impact loading on natural bone and the patellar prosthesis and may be accompanied by an audible crepitus. When planning the position of the femoral prosthesis, the surgeon must determine the appropriate positioning of the distal edge of the prosthesis to allow for a smooth transition to the condyles. This positioning is difficult to achieve without iterative trialing as there is no visual landmark to align to ensuring a smooth transition.

Therefore, there exists a need for improved patellofemoral implants and a method for sizing the components of the same.

BRIEF SUMMARY OF THE INVENTION

A first aspect of the present invention is a femoral implant for articulation with a patella or a patellar implant, including a body having an articular surface defining a trochlear groove, wherein the trochlear groove is defined by a first trochlear radius at a first location along the trochlear groove and by a second trochlear radius at a second location along the trochlear groove, the first radius being different than the second radius.

In other embodiments according to this first aspect, the first location may be proximal to the second location along the trochlear groove, and the first trochlear radius may be greater than the second trochlear radius. The first trochlear radius may be measured normal to a tangent to a trochlear groove nadir path at the first location, and the second trochlear radius may be measured normal to a tangent to the trochlear groove nadir path at the second location. A rate of trochlear radius reduction from the first trochlear radius to the second trochlear radius may define a trajectory of a patella or patellar implant over the femoral implant such that the patella or patellar implant contacts the trochlear groove nadir path at the first location and does not contact the trochlear groove nadir path at the second location. The rate of trochlear radius reduction may be constant.

A kit may include the above-described femoral implant and a patellar implant. In an extension configuration the patellar implant may align with the trochlear groove at the first location, and in a flexion configuration the patellar implant may align with the trochlear groove at the second location. In the extension configuration the patellar implant may contact the trochlear groove nadir path at the first location. In the extension configuration the patellar implant may contact the femoral implant at a single point or a single surface. In the flexion configuration the patellar implant may not contact the trochlear groove nadir path at the second location. In the flexion configuration the patellar implant may contact the femoral implant at two points or at two surfaces. In the extension configuration a posterior surface of the patellar implant may contact the trochlear groove nadir path at the first location, and in the flexion configuration lateral and medial surfaces of the patellar component may contact the trochlear groove at the second position. The trochlear groove may be defined by a third trochlear radius at a third location along the trochlear groove that is proximal to the first location, the third trochlear radius being greater than the first trochlear radius such that the patellar implant is guided into the trochlear groove when moved from the third location toward the first location during flexion.

The first location may be proximal to the second location along the trochlear groove, and the first trochlear radius may be greater than the second trochlear radius. The patellar implant may have an articular surface defined by a patellar radius, the patellar radius being less than or substantially equal to the first trochlear radius and greater than the second trochlear radius. The articular surface of the patellar implant may be substantially spherical. The first trochlear radius may be measured normal to a tangent to a trochlear groove nadir path at the first location, and the second trochlear radius may be measured normal to a tangent to the trochlear groove nadir path at the second location. A rate of trochlear radius reduction from the first trochlear radius to the second trochlear radius may define a trajectory of the patellar implant over the femoral implant such that the patellar implant contacts the trochlear groove nadir path at the first location and does not contact the trochlear groove nadir path at the second location. The rate of trochlear radius reduction may be constant.

A second aspect of the present invention is a method of trialing a femoral implant with a patella or a patellar implant including the steps of installing the femoral implant described above to a femur, and causing relative movement between the femoral implant and a patella or a patellar implant from an extension configuration in which the patella or the patellar implant aligns with the trochlear groove at the first location to a flexion configuration in which the patella or the patellar implant aligns with the trochlear groove at the second location.

In other embodiments according to this second aspect, the step of causing relative movement may include contacting the patella or the patellar implant with the trochlear groove nadir path at the first location. The step of causing relative movement may further include contacting the patella or the patellar implant with lateral sides of the trochlear groove and with the trochlear groove nadir path at another location between the first and second locations. The step of causing relative movement may further include contacting lateral and medial surfaces of the patella or the patellar component with lateral sides of the trochlear groove at the second location, such that the patella or the patellar implant does not contact the trochlear groove nadir path at the second location.

The step of causing relative movement may include moving the patella or the patellar component along a trajectory over the femoral implant such that the patella or patellar implant contacts the trochlear groove nadir path at the first location and does not contact the trochlear groove nadir path at the second location. The step of causing relative movement may include moving the patella or the patellar component along a trajectory over the femoral implant such that in the extension configuration the patellar implant contacts the femoral implant at a single point or a single surface and such that in the flexion configuration the patellar implant contacts the femoral implant at two points or at two surfaces.

The method may further include a step of installing a patellar implant to a patella; wherein the patellar implant has an articular surface defined by a patella radius, the patellar radius being less than or substantially equal to the first trochlear radius and greater than the second trochlear radius. The step of causing relative movement may include contacting the patellar implant with the trochlear groove nadir path at the first location. The step of causing relative movement may further include contacting the patellar implant with lateral sides of the trochlear groove and with the trochlear groove nadir path at another location between the first and second locations. The step of causing relative movement may further include contacting lateral and medial surfaces of the patellar component with lateral sides of the trochlear groove at the second location, such that the patellar implant does not contact the trochlear groove nadir path at the second location. The step of causing relative movement may include moving the patellar component along a trajectory over the femoral implant such that patellar implant contacts the trochlear groove nadir path at the first location and does not contact the trochlear groove nadir path at the second location. The step of causing relative movement may include moving the patellar component along a trajectory over the femoral implant such that in the extension configuration the patellar implant contacts the femoral implant at a single point or a single surface and such that in the flexion configuration the patellar implant contacts the femoral implant at two points or at two surfaces.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIG. 2A is a cross-sectional view of the patellofemoral implant in FIG. 1 at a position along line A-A;

FIG. 2B is a exploded cross-sectional view of the patellofemoral implant in FIG. 2A;

FIG. 4A is cross-sectional view of the patellofemoral implant in FIG. 3 at a position along line 4-4;

FIG. 4B is a cross-sectional view of the patellofemoral implant in FIG. 4A at a position along line B-B;

FIG. 5A is cross-sectional view of the patellofemoral implant in FIG. 3 at a position along line 5-5;

FIG. 5B is a cross-sectional view of the patellofemoral implant in FIG. 5A at a position along line C-C;

FIG. 6A is cross-sectional view of the patellofemoral implant in FIG. 3 at a position along line 6-6;

FIG. 6B is a cross-sectional view of the patellofemoral implant in FIG. 6A at a position along line D-D;

DETAILED DESCRIPTION

In describing preferred embodiments of the disclosure, reference will be made to directional nomenclature used in describing the human body. It is noted that this nomenclature is used only for convenience and that it is not intended to be limiting with respect to the scope of the invention.

As used herein, when referring to bones or other parts of the body, the term "anterior" means toward the front part or the face and the term "posterior" means toward the back of the body. The term "medial" means toward the midline of the body and the term "lateral" means away from the midline of the body. The term "superior" means closer to the heart and the term "inferior" means more distant from the heart.

Figure 1:
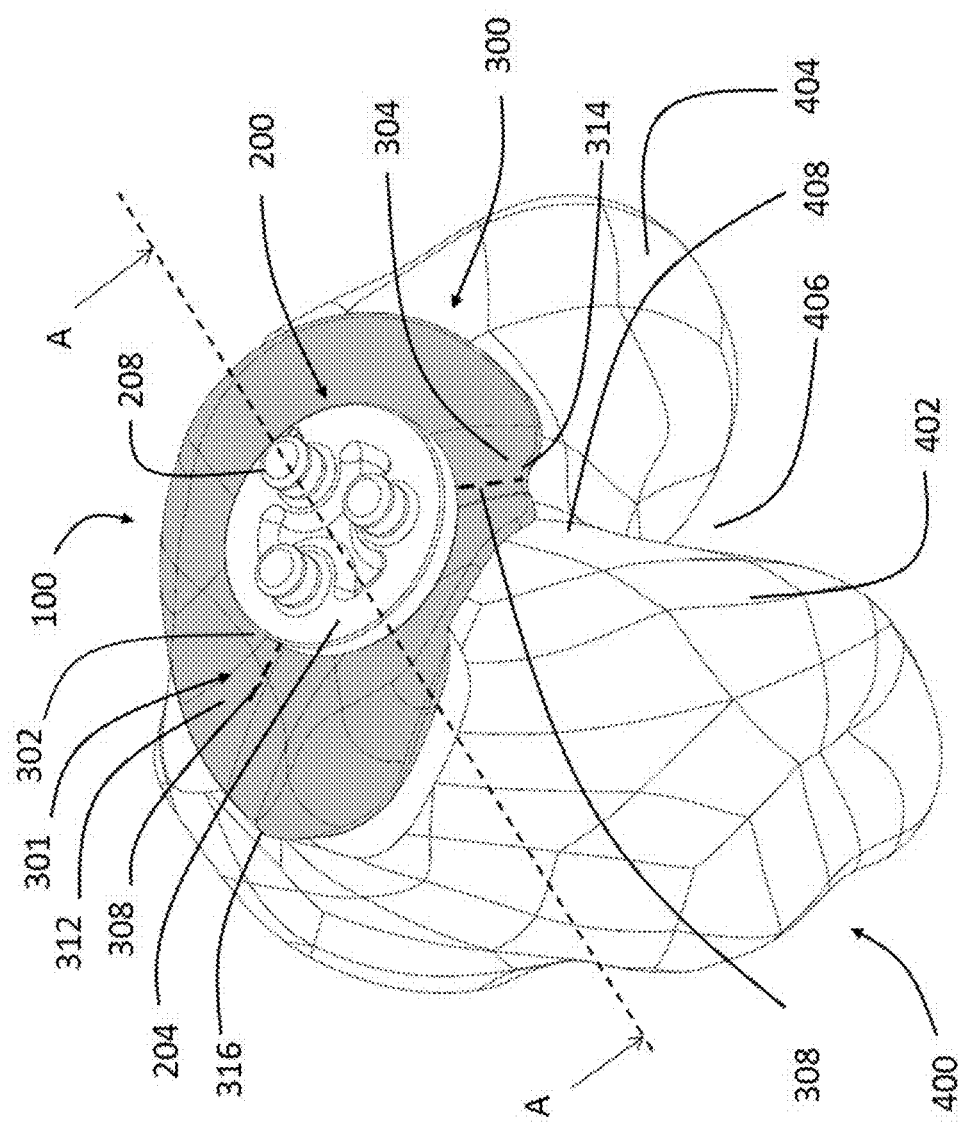
FIG. 1 is a perspective view of a patellofemoral implant with a femoral component and a patellar component in accordance with an embodiment of the present invention.

Referring to FIG. 1, there is shown a perspective view of a patellofemoral implant or kit 100 having a patellar component or implant 200 and a femoral component or implant 300 that is implanted over a femoral bone 400. Femoral component 300 generally includes a body having a curved articular surface that defines a trochlear groove 301 having a radius that narrows as groove 301 moves from a proximal-anterior location 302 to a distal-posterior location 304.

Trochlear groove 301 is defined by a first trochlear radius at a first location therealong and by a different second trochlear radius at a second location therealong, as described in more detail below. A substantially flat surface 312 located proximal to proximal-anterior location 302 provides laxity during patellar articulation and guides patellar component 200 into trochlear groove 301. This portion of femoral component 300 transitions into trochlear groove 301 to guide patellar component 200 into trochlear groove 301 during flexion.

Patellar component 200, as shown in FIG. 1, generally tracks along a path of trochlear groove 301 that extends between proximal-anterior location 302 and distal-posterior location 304. FIG. 1 depicts patellar component 200 at mid-flexion. Femoral bone 400 shown in FIG. 1 includes a lateral condyle 402, a medial condyle 404 and an intercondylar notch 406. Bone section 408 adjacent to a distal edge 314 of femoral component 300 represents the first bone contact surface for patellar component 200 upon extending distally past femoral component 300. The articular surface of femoral component 300 at distal edge 314 is flush with the surface of natural bone 400 to ensure smooth transition of patellar component 200 from femoral component 300 to the bone 400. That is, the surgeon can plan this transition by aligning the distolateral edge of femoral component 300 to be flush to native cartilage.

FIGS. 2A and 2B show cross-sectional views of patellofemoral implant 100 along line A-A of FIG. 1. FIG. 2A depicts patellar component 200 located in trochlear groove 301 of femoral component 300, whereas FIG. 2B shows an exploded view of patellar component 200 and femoral component 300. Patellar component 200 has a substantially spherical articulating surface 206 configured to contact a surface 310 of trochlear groove 301. An opposite posterior surface 204 of patellar component 200 includes one or more anchor pins 208 to attach patellar implant 200 to bone, i.e. the natural patella. As more fully explained below, location and surface area of the articulating surface 206 contact area will vary during patellar articulation. For example, as shown in FIG. 2A, a substantial portion of articulating surface 206, including an articulating surface center 210 is in contact with trochlear groove surface 310. As previously indicated, location of patellar component 200 on femoral implant 300 corresponds to patellar component 200 location at mid-flexion in FIG. 2A. A trochlear groove radius 306 and a patellar radius 202 are measured with reference to a central longitudinal axis L1 along a transverse plane. As best shown in FIG. 2A, patellar radius 202 and trochlear groove radius 306 are substantially the same when patellar component 200 is located at mid-flexion. This ensures that a substantial portion of the articular surface 210 contacts trochlear groove surface 310.

Figure 3:
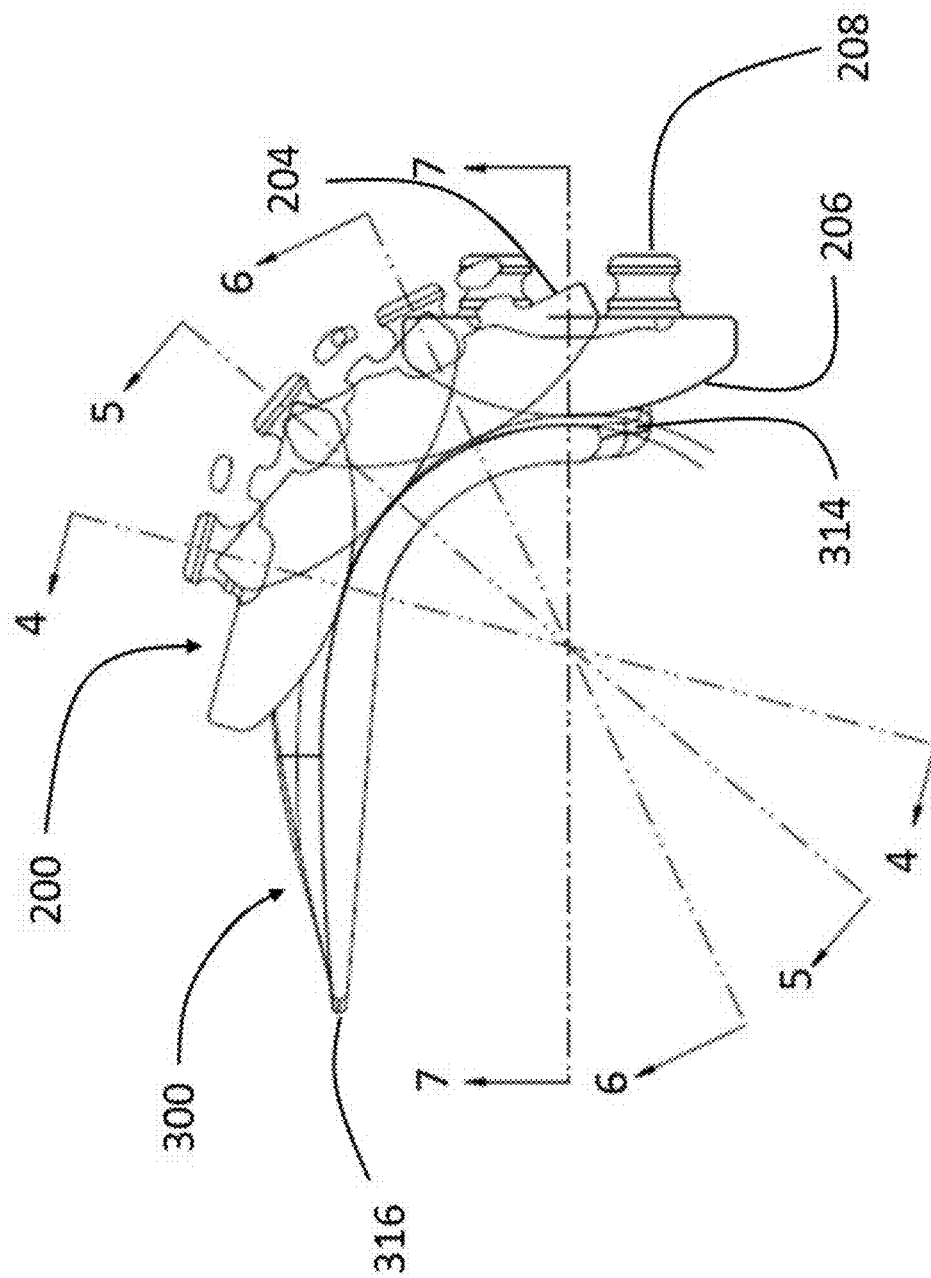
FIG. 3 is a side elevation view of the patellar component at different positions along the femoral component of the patellofemoral implant shown in FIG. 1.

Referring now to FIG. 3, there is shown a side elevation view of patellofemoral implant 100 with patellar implant 200 located at various positions along the femoral component 300. Multiple positions shown here correspond to the trajectory of patellar implant 200 from extension to deep-flexion representing a patellar range of motion.

FIG. 4A shows a transverse cross-sectional view of patellar component 200 along line 4-4 of FIG. 3. In this first location, patellar component 200 is located at a proximal anterior location of the trochlear groove 301 representing a patella position in an extension configuration of implant 100. Trochlear groove radius 306a at this first location is greater than patellar radius 202 in this position and therefore provides maximum patellar laxity in a medial-lateral direction. Trochlear groove radius 306a is measured in the plane depicted in FIG. 4A. That is, radius 306a is measured in a plane that is normal to a tangent line to a trochlear groove nadir path 308, or low point of trochlear groove 301, at this first location. Consequently, a posterior surface of patellar articulating surface 206 contacts trochlear groove surface 310 at the trochlear groove nadir path along transverse plane 4-4. This contact can be at a single point or at a single surface coinciding with the trochlear groove nadir path. FIG. 4B depicts another cross-sectional view of patellar component 200 along a sagittal plane B-B through trochlear groove nadir path 308 shown in FIG. 4A. As best seen in FIG. 4A, patella component 200 contacts trochlear groove nadir path 308 in this position because trochlear groove radius 306 is greater than patellar radius 202.

Referring now to FIG. 5A, there is show another cross-sectional view of patellofemoral implant 100 along line 5-5 of FIG. 3 in which patellar implant 200 is located distal to the previous position shown in FIG. 4A, indicating a patella motion from extension to flexion. In this position, trochlear groove radius 306b is narrower than trochlear groove radius 306a of the previous location, but trochlear groove radius 306b is still larger than the patellar radius 202. Patellar surface 206 continues to contact the trochlear groove nadir path of trochlear groove surface 310, as best seen in cross-section C-C along a sagittal plan through trochlear groove nadir path 308 depicted in FIG. 5B.

FIG. 6A shows a yet another cross-sectional view along a transverse plane represented by line 6-6 of FIG. 3. In this location, patellar component 200 corresponds to a patella in mid-flexion. Trochlear groove radius 306c is now narrower than trochlear groove radius 306b and is substantially equal to patellar radius 202 in this position. As best shown in a cross-sectional view along line D-D of FIG. 6A, patellar articulating surface 206 continues to contact trochlear groove nadir path 308 and indeed a large portion of trochlear groove surface 310 in this position.

Figure 7A:
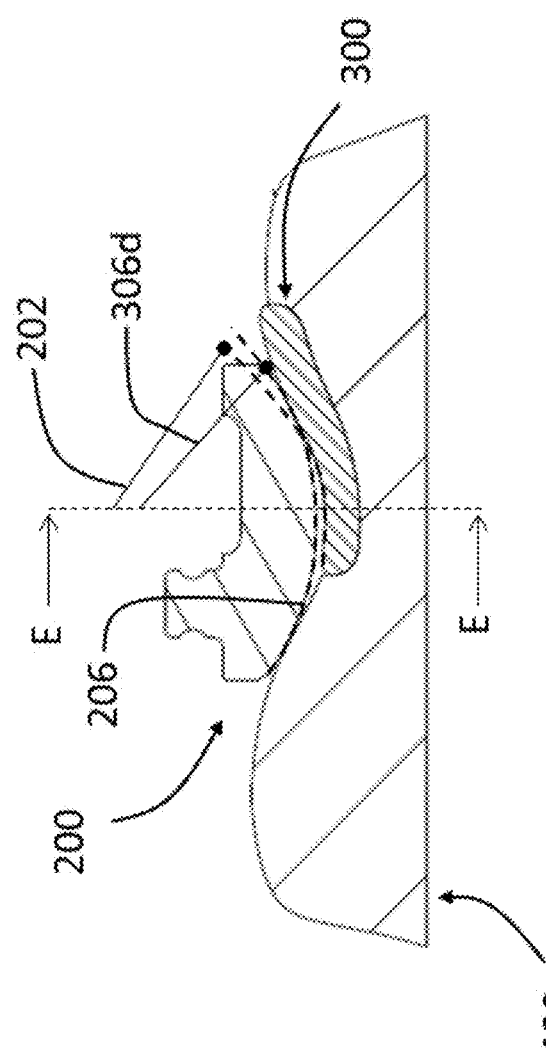
FIG. 7A is cross-sectional view of the patellofemoral implant in FIG. 3 at a position along line 7-7.
Figure 7B:
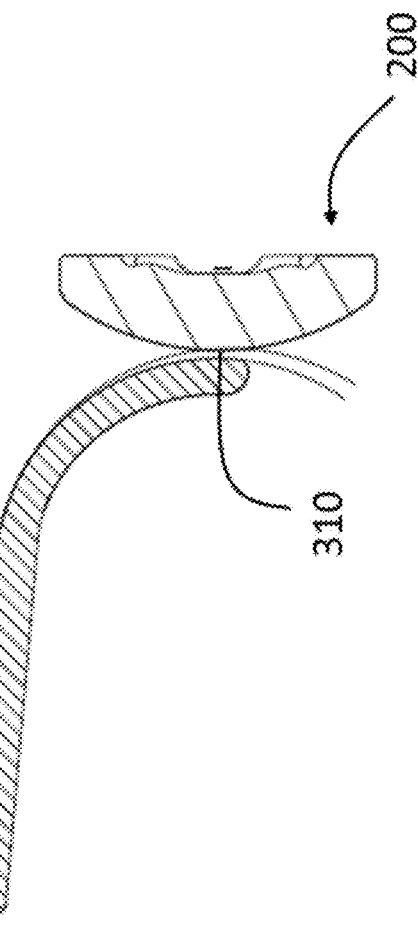
FIG. 7B is a cross-sectional view of the patellofemoral implant in FIG. 7A at a position along line E-E.

Referring now to FIG. 7A, there is shown a cross-sectional view of patellar component 200 in deep flexion taken along line 7-7 in FIG. 3. Trochlear groove radius 306d is now less than patellar radius 202 which forces patellar articulating surface 206 to separate from trochlear groove nadir path 308 of trochlear groove surface 310 so that patellar component 200 does not contact the trochlear groove nadir path at this location. FIG. 7B shows a cross-sectional view along a sagittal plane E-E of FIG. 7A and further illustrates the separation of patellar articulating surface 206 from the trochlear groove nadir path of trochlear groove surface 310. In deep flexion, the narrow trochlear groove radius 306d causes patellar component 200 to lift away from the trochlear groove nadir path such that only medial and lateral surfaces of patellar component 200 are in contact with femoral component 300. That is, in this flexion configuration, patellar component 200 contacts femoral component 300 at two points or at two surfaces, both being apart from the trochlear groove nadir path.

Further proximal to distal movement of patellar component 200, i.e., flexion beyond deep-flexion as shown in FIG. 7A, will result in patellar component 200 contact with natural bone (shown in FIG. 1). Lateral and medial sides of patellar articular surface 206 will contact lateral condyle 402 and medial condyle 404 when patellar component 300 transitions to bone 400. As seen in 7A, lateral and medial articulating surfaces of patellar component 200 are in contact with femoral component 300 at deep flexion and as such the narrowing trochlear groove 301 ensures that a similar contact profile, i.e., a dual surface contact, is maintained when patellar component 200 transitions to bone 400. The dual surface contact from femoral component 300 to natural bone 400 provides a smooth transition and maintains an arcuate path through the patellar range of motion.

Figure 8:
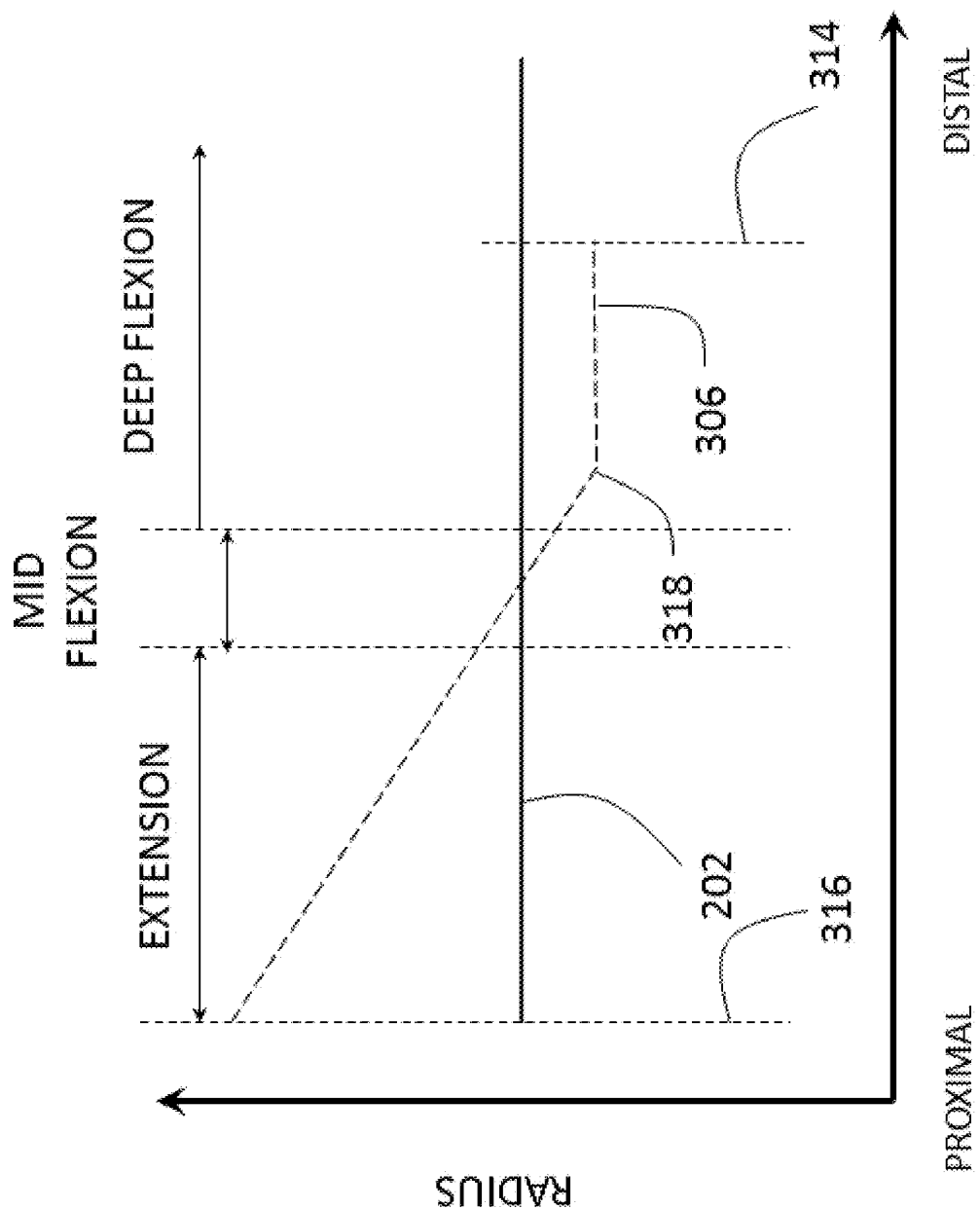
FIG. 8 is a graph showing a radius of the patellar component and a radius of a trochlear groove of the femoral component of the patellofemoral implant of FIG. 1.
Figure 9:
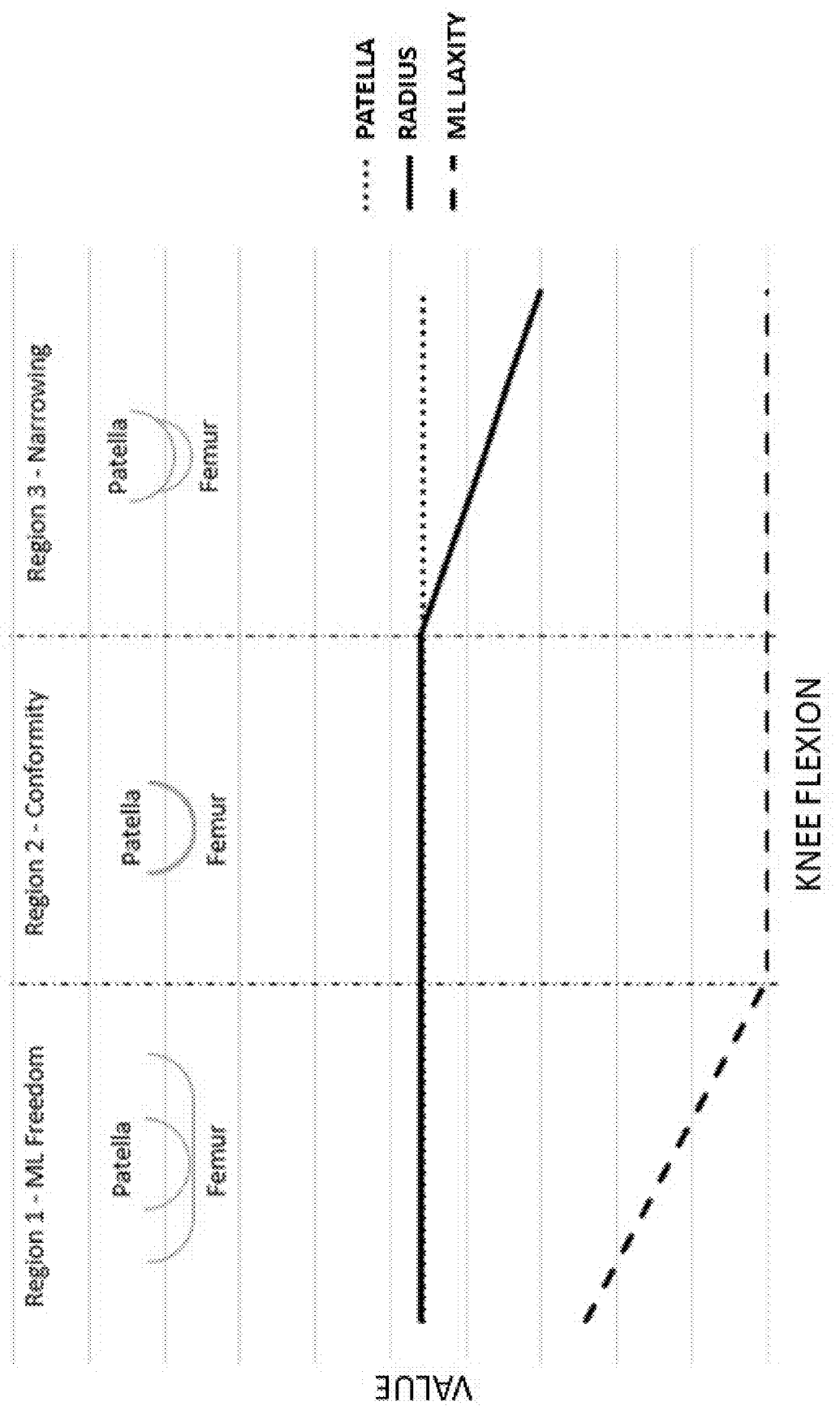
FIG. 9 is a graph showing a relationship between the radius of a patellar component, the radius of a trochlear groove and medial lateral laxity of the femoral component according to another embodiment of the present invention.

FIG. 8 shows a graph plotting patellar radius 202 and trochlear groove radius 306 across a patellar range of motion from extension to deep flexion according to one embodiment of the present invention. Patellar radius 202 remains constant, whereas trochlear groove radius 306 reduces during extension, mid-flexion and into deep flexion. Trochlear groove radius 306 is greatest at proximal edge 316 and least at distal edge 314. Through extension, trochlear groove radius 306 is greater than patellar radius 202 and ensures that patellar articulating surface 206 is in contact with the trochlear groove nadir path of trochlear groove nadir path 308 as shown in region 1 depicted in FIG. 9. Region 1 corresponds to maximum medial-lateral laxity as illustrated in FIG. 9. During mid-flexion, trochlear groove radius 306 continues to decrease and is generally equal to patellar radius 202 as shown in region 2 of FIG. 9. This allows medial and lateral sides of patellar articulating surface 206 to move into contact with trochlear groove 301. Trochlear groove 301 continues to narrow as patellar component 200 enters into deep-flexion, whereby the patellar radius 202 significantly exceeds trochlear groove radius 306 and cause patellar articulating surface 206 to lift away from the trochlear groove nadir path of trochlear groove nadir path 308. At the narrowest trochlear groove radius 306 corresponding to location 318, only the lateral and medial surfaces of the patellar component 200 are in contact with the trochlear groove 301 as shown in region 3 of FIG. 9. Medial-lateral patellar surface contact with femoral component 300 continues until distal edge 314 and further continues into transition of patellar component 200 onto bone section 408. Consequently, there is no abrupt transition of patellar component 200 from femoral component 300 to natural bone 400 because the medial and lateral patellar surface contact can smoothly slide from the femoral component 300 to medial and lateral condyle 402, 404.

While trochlear groove radius 306 reduction is linear and constant in FIG. 8, other embodiments may have different rates of reduction. Whereas the minimum trochlear groove radius 306 is at location 308 in this embodiment, other embodiments may have minimum trochlear radius at locations distal or proximal to 318. The rate of trochlear groove radius reduction and location of minimum trochlear groove radius 306 may be controlled to obtain a desired patella range of motion. For example, providing a steep rate of trochlear groove radius reduction and locating minimum trochlear groove radius 306 proximal to location 318 will ensure that patellar component 200 is lifted from trochlear groove nadir path 308 prior to deep flexion. That is, the rate of trochlear radius reduction defines a trajectory of the patellar component 200 over femoral component 300, and specifically over the trochlear groove nadir path of femoral component 300. Patellar components generally have a constant radius and may be selected as disclosed in U.S. application Ser. No. 15/227,433, the disclosure of which is hereby incorporated by reference herein as if fully set forth herein.

Another aspect of the present invention is a method for sizing patellofemoral implant 100 to ensure smooth transition of patellar component 200 from femoral component 300 to natural bone. The method includes the steps of sizing a narrowing trochlear groove 301 on femoral component 300 such that a radius of trochlear groove 301 is greater than the patellar radius at an extension position and transitions to being less than the patellar radius as patellar component 200 transitions from the femoral component to natural bone, as best shown in FIG. 8. As way of example, but not limitation, in one embodiment an articulating surface of a patella or a patellar implant may have a radius of 22.3 mm. The trochlear groove radius 306 may be configured to narrow from 66 mm to 15 mm with a linear reduction rate shown in FIG. 8. As more fully described above, the rate of reduction and location of the narrowest trochlear groove radius 306 may be configured to obtain a desired patella range of motion.

A method of trialing femoral component 300 with a patella or patellar component 200 includes installing the femoral component 300 to a femur, and causing relative movement between the femoral component 300 and the patella or patellar component 200 from an extension configuration to a flexion configuration. As explained above, in the extension configuration, the patella or the patellar component 200 aligns with trochlear groove 301 at a first location similar to that shown in FIGS. 4A and 4B. Also, in the flexion configuration, the patella or patellar component 200 aligns with trochlear groove 301 at a second location similar to that shown in FIGS. 7A and 7B.

The trialing method causes operation of patellofemoral implant or kit 100 as described above. In the event that a patellar component 200 is not used and the natural patella is instead maintained, femoral component 300 can be used alone with the natural patella. When patellar component 200 is used, the method can involve a step of installing patellar component 200 to a patella.

While a patellofemoral implant is described in these embodiments, narrowing grooves or slots of the present invention may be used with any implant having two or more sliding components to ensure smooth transition from one component of the implant to native bone. Implants containing narrowing grooves or slots of the present invention may be made polymer such as PEEK, carbon fiber reinforced PEEK, PAEK, UHMWPE, metals, ceramics, combinations of the foregoing, or other suitable materials that are biocompatible and possess sufficient strength and rigidity. Near net shape casting, subtractive manufacturing techniques, and additive manufacturing techniques such as 3D printing may be used to fabricate implants with narrowing groove of the present invention.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A kit comprising:
 a femoral implant having a body with an articular surface defining a trochlear groove, the trochlear groove defining a trochlear groove nadir path extending along the trochlear groove, wherein the trochlear groove is defined by a first trochlear radius at a first location along the trochlear groove and by a second trochlear radius at a second location along the trochlear groove, the first radius being different than the second radius, the first trochlear radius being measured normal to a tangent to the trochlear groove nadir path at the first location, and the second trochlear radius being measured normal to a tangent to the trochlear groove nadir path at the second location, and a patellar implant, wherein in an extension configuration the patellar implant aligns with the trochlear groove at the first location, and wherein in a deep flexion configuration the patellar implant aligns with the trochlear groove at the second location such that in the deep flexion configuration the patellar implant does not contact the trochlear groove nadir path at the second location.

2. The kit of claim 1, wherein in the extension configuration the patellar implant contacts the trochlear groove nadir path at the first location.

3. The kit of claim 2, wherein in the extension configuration the patellar implant contacts the femoral implant at a single point or a single surface.

4. The kit of claim 1, wherein in the deep flexion configuration the patellar implant contacts the femoral implant at two points or at two surfaces.

5. The kit of claim 1, wherein in the extension configuration a posterior surface of the patellar implant contacts the trochlear groove nadir path at the first location, and in the deep flexion configuration lateral and medial surfaces of the patellar implant contact the trochlear groove at the second location.

6. The kit of claim 1, wherein the trochlear groove is defined by a third trochlear radius at a third location along the trochlear groove that is proximal to the first location, the third trochlear radius being greater than the first trochlear radius such that the patellar implant is guided into the trochlear groove when moved from the third location toward the first location during flexion.

7. The kit of claim 1, wherein the first location is proximal to the second location along the trochlear groove, and the first trochlear radius is greater than the second trochlear radius.

8. The kit of claim 7, wherein the patellar implant has an articular surface defined by a patellar radius, the patellar radius being less than or substantially equal to the first trochlear radius and greater than the second trochlear radius.

9. The kit of claim 8, wherein the articular surface of the patellar implant is substantially spherical.

10. The kit of claim 1, wherein a rate of trochlear radius reduction from the first trochlear radius to the second trochlear radius defines a trajectory of the patellar implant over the femoral implant such that the patellar implant contacts the trochlear groove nadir path at the first location and does not contact the trochlear groove nadir path at the second location.

11. The kit of claim 10, wherein the rate of trochlear radius reduction is constant.

12. The kit of claim 7, wherein the patellar implant aligns with the trochlear groove at the second location in a mid-flexion configuration, the third location being proximal to the second location.

* * * * *